United States Patent [19]

Irikura

[11] 4,042,594

[45] Aug. 16, 1977

[54] THE HYPOLIPIDEMIC AGENT, 4-(4-CHLOROBENZYLOXY)-BENZYL NICOTINATE AND PREPARATION THEREOF

[75] Inventor: Tsutomu Irikura, Tokyo, Japan

[73] Assignee: Kyorin Pharmaceutical Co., Ltd., Tokyo, Japan

[21] Appl. No.: 701,015

[22] Filed: June 30, 1976

[30] Foreign Application Priority Data

Nov. 8, 1975 Japan .............................. 50-134445

[51] Int. Cl.$^2$ .................................... C07D 213/55
[52] U.S. Cl. .............................. 260/295.5 R; 424/266
[58] Field of Search ............................ 260/295.5 R

[56] References Cited

U.S. PATENT DOCUMENTS 3,992,543  11/1976  Massaroli ..................... 260/295.5 R

FOREIGN PATENT DOCUMENTS 1,312,775  7/1970  United Kingdom ......... 260/295.5 R

*Primary Examiner*—Alan L. Rotman
*Attorney, Agent, or Firm*—Armstrong, Nikaido & Marmelstein

[57] ABSTRACT

This invention relates to novel 4-(4'-chloro-benzyloxy)-benzyl nicotinate and its salts, and to methods of preparing thereof.

2 Claims, No Drawings

THE HYPOLIPIDEMIC AGENT, 4-(4-CHLOROBENZYLOXY)-BENZYL NICOTINATE AND PREPARATION THEREOF

DETAILED DESCRIPTION OF THIS INVENTION:

The compound can be indicated by the following formula (III):

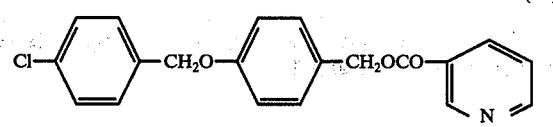

The preparation of the compound can be illustrated as follows:

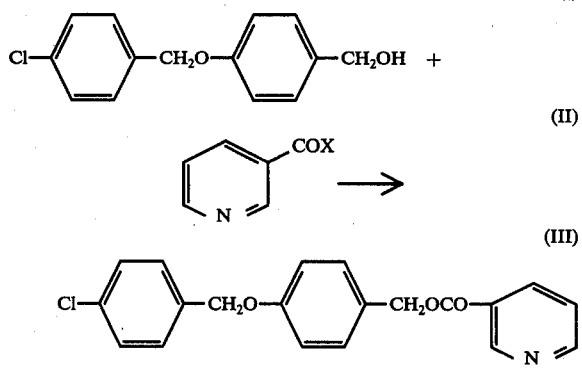

wherein X represents chlorine or bromine atom.

The compound of this invention is prepared by the reaction of a part of 4-(4'-chlorobenzyloxy)benzyl alcohol (I) and a part of nicotinoyl halide (II) or its hydrohalide in the presence of a base.

The reaction is conducted in an anhydrous solvent, for example, benzene, toluene, dimethylformamide, and tetrahydrofuran. The reaction proceeds smoothly in the presence of a base, such as pyridine, dimethylaniline or triethylamine.

The starting material (I) of this invention is a new compound. The compound (I) is obtained easily from ethyl 4-(4'-chlorobenzyloxy)benzoate by reduction with lithium aluminum hydride in anhydrous tetrahydrofuran, or from 4-(4'-chorobenzyloxy)benzaldehyde by reduction with sodium borohydride in ethanol.

Salts of the compound of this invention are primarily therapeutically acceptable acid addition salts with inorganic or organic acids. Suitable inorganic acids are, for example, mineral acids, such as hydrochloric or hydrobromic acid, or sulfuric or phosphoric acid. Organic acids are, for example, acetic, propionic, tartaric, citric acid and the like.

The present compound induced by this invention possess some excellent hypolipidemic actions and is useful as a hypolipidemic agent.

1. Prophylactic effect

DDN strain male mice aged 3 weeks were divided into three groups and fed as follows;

i. Cholesterol and cholic acid were mixed with the powder diet (CE-2) in 1.0% or 0.2% respectively (basal diet).

ii. The present compound was mixed with the basal diet in 0.05%.

iii. Clofibrate was mixed with the basal diet in 0.1% as a standard drug control.

Three groups of 10 each were fed for 8 days above diet respectively. On the 8th day, mice were sacrificed and serum cholesterol was determined.

As shown in Table 1, the present compound significantly suppressed the elevation of the serum cholesterol level in comparison with control ($p<0.001$) and was more effective than that of clofibrate.

Table 1

| Compound | Drug ingested mg/kg/day | Serum cholesterol mg/dl | Relative % |
|---|---|---|---|
| Control | — | 446.4±24.7 | (100) |
| Present compound | 113.9 | 257.8±24.5* | 57.8 |
| Clofibrate | 197.7 | 366.9±30.4 | 82.2 |

*Significantly different from control ($p<0.001$)

2. Effects on serum lipids and liver weight of normal rats.

Male rats of Wistar strain, weighing 160 - 190g, were divided into 3 groups as follows:

i. Control group (0.5% CMC)
ii. Present compound treated group
iii. Clofibrate treated group Each drug (100 mg/kg/day) which suspended in 0.5% CMC was administered orally 9 times during 10 days. At 4 hours after final administration, fasting rats were sacrificed and blood was collected from jugular vein. Serum lipids were determined and livers were weighed.

As shown in Table 2, the present compound reduced serum cholesterol, triglycerid and phospholipid. These reducible actions significantly differed from control ($p<0.001$, $p<0.025$, $p<0.001$, respectively). The present compound has similar reducible potency to clofibrate on serum cholesterol and phospholipid, but serum triglycerid level in clofibrate treated group, on the contrary, increased more than that of control. In addition, the present compound slightly enlarged rat liver, but clofibrate enlarged to 128% and significantly differed from control ($p<0.001$).

Table 2

| Compound | Liver weight (g) (Relative % to b.w.) | Serum Cholesterol mg/dl | Triglycerid mg/dl | Phospholipid mg/dl |
|---|---|---|---|---|
| Control | 3.12±0.07 (100) | 65.1±3.0 (100) | 35.2±2.3 (100) | 91.6±3.1 (100) |
| Present compound | 3.28±0.04 (105.1) | 44.4±2.6* (68.2) | 25.8±2.7** (73.3) | 63.1±4.1* (68.9) |
| Clofibrate | 3.98±0.07* (127.6) | 43.3±3.1* (66.5) | 39.3±4.3 (111.7) | 64.9±3.6* (70.9) |

The values represent mean ±S.E.
Numbers in parentheses indicate relative % to control.
Significantly different from control;
*$p<0.001$,
**$p<0.025$

ACUTE TOXICITY

The acute toxicity of present compound was investigated in mice (10 ddN strain male mice weighing 23 - 27g) by p.o. administration. Treated animals were housed in groups of same doses and observed daily for a period of 72 hr. Statistical calculations followed the method of Litchfield and Wilcoxon. In mice, LD$_{50}$ of the present compound by p.o. administration was 3000 mg/kg (2069 – 4350).

The following example illustrates this invention but does not limit it:

EXAMPLE

To a mixture of 1.2g of 4-(4'-chlorobenzyloxy)benzyl alcohol, 1.0g of triethylamine and 25 ml of anhydrous benzene was added 0.9g of hydrochloride of nicotinoyl chloride at 10° C. The whole mixture was stirred at room temperature for 3 hours. The reaction mixture was washed with water. The organic layer was dried over sodium sulfate and then concentrated in vacuo to give a crystalline residue. The residue was recrystallized from ethanol to give 1.2g of 4-(4'-chlorobenzyloxy)-benzyl nicotinate, mp 101°-2° C.

Analysis, Calcd. for $C_{20}H_{16}NO_3Cl$: C, 67.90; H, 4.56; N, 3.96. Found: C, 67.91; H, 4.37; N, 3.97.

What is claimed is:

1. 4-(4'-Chlorobenzyloxy)benzyl nicotinate having the following formula:

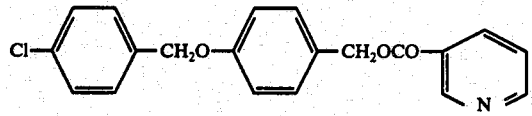

2. A pharmaceutically acceptable acid addition salt of the compound of claim 1.